United States Patent
Wu

(10) Patent No.: US 10,702,476 B2
(45) Date of Patent: Jul. 7, 2020

(54) MICROPARTICLE FORMULATIONS OF ADENOSINE RECEPTOR ANTAGONISTS FOR TREATING CANCER

(71) Applicant: Phosphorex, Inc., Hopkinton, MA (US)

(72) Inventor: Bin Wu, Lexington, MA (US)

(73) Assignee: PHOSPHOREX, INC., Hopkinton, MA (US)

( * ) Notice: Subject to any disclaimer, the term of this patent is extended or adjusted under 35 U.S.C. 154(b) by 0 days.

(21) Appl. No.: 16/103,226

(22) Filed: Aug. 14, 2018

(65) Prior Publication Data

US 2019/0046448 A1    Feb. 14, 2019

Related U.S. Application Data

(60) Provisional application No. 62/545,290, filed on Aug. 14, 2017.

(51) Int. Cl.

| | | |
|---|---|---|
| *A61K 9/16* | (2006.01) | |
| *A61P 35/00* | (2006.01) | |
| *A61K 31/519* | (2006.01) | |
| *A61K 9/00* | (2006.01) | |
| *A61P 37/00* | (2006.01) | |

(52) U.S. Cl.
CPC .......... *A61K 9/1647* (2013.01); *A61K 9/0024* (2013.01); *A61K 9/1635* (2013.01); *A61K 9/1652* (2013.01); *A61K 31/519* (2013.01); *A61P 35/00* (2018.01); *A61P 37/00* (2018.01)

(58) Field of Classification Search
None
See application file for complete search history.

(56) References Cited

U.S. PATENT DOCUMENTS 8,993,653 B2 * 3/2015 Kaya ............... C08G 63/78
                                                 264/328.1
2009/0208550 A1    8/2009 Cronstein et al.
2013/0324503 A1   12/2013 Payami et al.

FOREIGN PATENT DOCUMENTS

| WO | 2016176558 A1 | 11/2016 | |
|---|---|---|---|
| WO | 2017189849 A1 | 11/2017 | |
| WO | WO-2017189849 A1 * | 11/2017 | ........... A61K 31/519 |

OTHER PUBLICATIONS

Honary, S. et al., "Effect of Zeta Potential on the Properties of Nano-Drug Delivery Systems—A Review (Part 1)", Tropical Journal of Pharmaceutical Research, vol. 12, Apr. 2013, 255-264.
Getts, D. R., et al., "Therapeutic Inflammatory Monocyte Modulation Using Immune-Modifying Microparticles," Sci Transl Med, 6, 219ra7 (2014).
Walter, E., et al., "Microparticle-mediated Transfection of Nonphagocytic Cells In Vitro," J. Drug Targeting, 10(1): 11-21 (2002).

* cited by examiner

*Primary Examiner* — Celeste A Roney
(74) *Attorney, Agent, or Firm* — Elmore Patent Law Group, P.C.; Carolyn S. Elmore; Darlene A. Vanstone

(57) ABSTRACT

The invention provides compositions comprising microparticles wherein the microparticles comprise at least one adenosine 2a receptor antagonist (A2ARA), at least one pharmaceutically acceptable polymer and at least one pharmaceutically acceptable negatively charged agent wherein the microparticles optionally have a highly negative zeta potential of less than about −40 mV. The invention also provides pharmaceutical compositions of the microparticles of the invention and methods of using the compositions of the invention to enhance an immune response in a patient in need thereof and as anti-cancer immunotherapy.

19 Claims, No Drawings

MICROPARTICLE FORMULATIONS OF ADENOSINE RECEPTOR ANTAGONISTS FOR TREATING CANCER

RELATED APPLICATION

This application claims the benefit of U.S. Provisional Application No. 62/545,290, filed on Aug. 14, 2017. The entire teachings of the above application are incorporated herein by reference.

The current invention relates to immunotherapy for the treatment of cancer, specifically it relates to the use of microparticles or nanoparticles of adenosine 2a receptor antagonists (A2ARA) to activate immune cells to kill tumor.

INTRODUCTION

Immunotherapy is rapidly emerging as a cancer treatment with high potential. Recent advances in immune checkpoint therapy have led to the FDA approval and successful launch of several products in treating various cancers. These new drug products are based on the blocking of the inhibitory pathways between tumors and tumor-infiltrated T cells.

Tumor microenvironment has an immunosuppressive nature, preventing immune cells from killing the tumors. Many of these immunosuppressive mechanisms in tumors are common to physiological immunoregulation in normal tissues and are critical in keeping the immune system under control to prevent autoimmunity. However, tumors take advantage of such physiological immunoregulatory mechanisms to protect their tissue from immune attack. As a result, these mechanisms become major obstacles for immunological cancer treatment. For example, CTLA-4 is a physiological mechanism that negatively regulates T cell activity by blocking a costimulatory signal through CD28-B7 interaction. PD-1 also provides a T cell inhibitory signal upon inter-action with its ligands, PD-L1 and PD-L2. The identification of immunosuppressive mechanisms in tumors led to FDA approval of anti-CTLA-4 and anti- PD-1 antibodies for cancer treatment.

Besides PD-1 and CTLA-4, there have been found other immune checkpoint molecules. For example, extracellular adenosine has been known as an inhibitor of immune functions. The generation of adenosine by CD73 also suppresses antitumor immune responses through the activation of A2A receptors on T cells and natural killer (NK) cells. A2A adenosine receptor (A2AR) is the predominantly expressed subtype in most immune cells. Stimulation of A2AR generally provides an immunosuppressive signal that inhibits activities of T cells (proliferation, cytokine production, cytotoxicity), NK cells (cytotoxicity), NKT cells (cytokine production, CD40L upregulation), macrophages/dendritic cells (antigen presentation, cytokine production), and neutrophils (oxidative burst). Indeed, the presence of elevated levels of extracellular adenosine in tumors has been found to play a significant role in the evasion of antitumor immune response. The adenosine-rich environment in tumors may induce T cells that are anergic to the tumor cells. Consistent with this change, A2AR stimulation induces immunoregulatory molecules such as CTLA-4 and PD-1 on T cells. Antigen-presenting cells (APCs) are also targets of adenosine. A2AR and A2BR seem to mainly target lymphoid cells and myeloid cells, respectively. The impact of adenosine-mediated immunosuppression seems to be persistent rather than transient because the outcome of adenosine exposure can induce M2-type tumor-associated macrophages, Treg cells, MDSC, and "anergic" effector T cells.

These facts indicate that extracellular adenosine is a negative immune checkpoint molecule that plays a significant role in establishing an immunosuppressive tumor microenvironment. Therefore, it is reasonable to target the adenosine-dependent pathway to improve cancer therapy. The blockade of A2AR and A2BR using antagonists can inactivate the adenosine-dependent immunosuppression. For example, recent reports demonstrated blockade of A2A receptors could enhance the efficacy of anti-PD-1 in treating cancer in combination therapies.

Monocytes and macrophages are essential components of the innate immune system. They comprise what was just recently recognized as a heterogenous family of professional phagocytic cells responsible for the recognition and clearance of pathogens and dead cells. Monocytes and macrophages play central roles in the initiation and resolution of inflammation, principally through phagocytosis, release of inflammatory cytokines, reactive oxygen species (ROS) and the activation of the acquired immune system. Monocytes and macrophages originate from a common myeloid progenitor cell in the bone marrow. Under normal circumstances, monocytes circulate in the bloodstream for a very brief time before undergoing spontaneous apoptosis.

Macrophages are large phagocytic cells and are found in almost every organ. They tend to constitute a highly heterogeneous pool with distinct biological activities that are influenced both by genetics and environment. Macrophages play a key role in cancer immunology. For example, immune cells such as tumor associated macrophages (TAMs) can represent up to 50% of a breast tumor mass. Macrophages can broadly be divided into two types: M1 (anti-tumor) and M2 (pro-tumor) macrophages. These subtypes may not be predetermined prior to recruitment but 'programmed' or 'educated' by the tumor microenvironment upon arrival. TAMs generally have M2 properties and promote tumor progression, metastasis, and resistance to chemotherapy. Clinically, a high tumor density of TAMs has been significantly associated with resistance to chemotherapy and a worse clinical outcome of human tumors. Recently, pharmaceutical compounds have been developed to target the pro-tumor effect of TAMs. These compounds have had a variety of effects including changing TAMs to M1 macrophages.

Macrophages originate from monocytes in response to differentiation factors such as granulocyte-macrophage colony-stimulating factor (GM-CSF), macrophage colony-stimulating factor (M-CSF), and colony-stimulating factor-1 (CSF-1). Comparative studies have demonstrated differences in gene expression between monocytes and macrophages and their different life spans. Unlike monocytes, macrophages have a long-life span, ranging from months to years. It is reported that super physiological doses of GM-CSF administered in the local tumor environment induces the production of sVEGFR-1 tumor-produced VEGF and angiogenesis. Fortuitously, GM-CSF recruits significantly more macrophages to these tumors than those untreated. At one time, this effect might be considered a detriment to tumor therapy as many studies have shown that removal of TAMs leads to a reduction in angiogenesis and metastases. But, because GM-CSF seems to either maintain the M1 macrophage phenotype recruited into the tumor, or because GM-CSF 're-educates' or 're-programs' the M2 TAMs back to an M1 phenotype, this suggests that an increase in M1 macrophages is beneficial and illustrates that influencing the M1/M2 polarity of macrophages provides an opportunity for the host immune cells to once again perform their initial role as tumor-fighting cells.

Because they play such central roles in immune-regulation, macrophages and monocytes can be exploited to deliver therapeutic agents. It would be beneficial use monocytes and macrophages as targeted sites for the delivery of A2AR antagonists to inhibit the immunosuppressive pathway associated with adenosine.

It is important to deliver A2AR antagonists to the tumor microenvironment. However, due to their lipophilicity, poor solubility, hydrolytic instability, and molecular size, the A2AR antagonists cannot be effectively delivered to the tumor microenvironment. None of currently available methods offers targeted delivery of A2AR antagonists specifically to the tumor microenvironment. In addition, there does not exist a method that provides sustained delivery of A2AR antagonists in the tumor microenvironment so that effector T cells can receive constant and continuous stimulating effect from the A2AR antagonists.

Therefore, it is the objective of the current invention to provide a pharmaceutical formulation that can be effectively taken up by monocytes and macrophages and subsequently transferred to the tumor microenvironment, providing sustained release of A2AR antagonists thereby increasing the capability of immune cells to kill cancerous tumors, for example.

SUMMARY

The invention provides compositions comprising microparticles wherein the microparticles comprise at least one adenosine 2a receptor antagonist (A2ARA), at least one pharmaceutically acceptable polymer and optionally, at least one pharmaceutically acceptable negatively charged agent wherein the microparticles have a negatively charged surface. The invention also provides pharmaceutical compositions of the microparticles of the invention and methods of using the compositions of the invention to enhance an immune response in a patient in need thereof and as anticancer immunotherapy.

DETAILED DESCRIPTION OF THE INVENTION

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

The invention provides compositions of microparticles for immunotherapy for the treatment of cancer wherein the microparticles can have increased targeting ability, bioavailability, solubility, and sustained release nature, comprising microparticles of at least one A2AR antagonist (A2ARA). The term "sustained delivery" or "sustained release" refer here to the delivery or release of A2ARA into a tumor microenvironment, for example, at a predetermined rate by maintaining an essentially constant drug level for a specific period of time. The terms "controlled release" and "extended release" retarded release, prolonged release, slow release ja rate controlled release are understood to be used for the same purpose.

One aspect of the invention provides a pharmaceutical formulation comprising at least one A2AR antagonist (A2ARA), an optional pharmaceutically acceptable negatively charged agent and a pharmaceutically acceptable polymer, wherein the pharmaceutically acceptable polymer encapsulates the A2ARA to form microparticles, wherein said microparticles have negatively charged surface.

As used herein, "pharmaceutically acceptable" includes those compounds, materials, compositions, and/or dosage forms which are, within the scope of sound medical judgment, suitable for medical or veterinary use when in contact with the tissues of human beings and animals, without causing excessive toxicity, irritation, allergic response, or other problems or complications, commensurate with a reasonable benefit/risk ratio. Preferably, a pharmaceutically acceptable material (e.g., polymer or microparticles/nanoparticles produced therefrom) is suitable or approved for human medical use.

Pharmaceutically acceptable polymers include, but are not limited to Polylactide (PLA), poly(lactide-co-glycolide) (PLGA), Poly-epsilon-caprolactone (PCL). Preferably the microparticles of the invention comprise PLGA. Preferably, the PLGA has an average molecular weight of from about 500 to about 1,000,000 Da, preferably from about 1,000 to about 50,000 Da. Preferably, the PLGA contains multiple negatively charged terminal groups.

As used herein the term "microparticles" is used generally to refer to particles having an effective average particle size in both the micron (μm) range and in the nanometer (nm) range. The term "microparticles" therefore includes "nanoparticles" and both terms may be used herein. The term "microparticle" is not intended to convey any specific shape limitation. Microparticles, include, but are not limited to those having a generally polyhedral or spherical geometry.

As used herein the term "encapsulates", "encapsulated", and the like when referring to the A2ARA being encapsulated by the polymer within the microparticles means that the A2ARA is more likely found within the microparticle than on the surface of the microparticle.

Preferably, the effective particles size of the microparticles of the invention are about 1 nm to about 10 μm. Preferably, the microparticles have an effective particle size that is about 10 microns or lower, preferably about 5 microns or lower, preferably about 3 microns or lower, preferably about 2 microns or lower, preferably about 900 nm or lower, preferably about 700 nm or lower, preferably about 600 nm or lower and preferably about 500 nm or lower.

By "an effective average particle size of less than about 5 microns", for example, it is meant that at least 50% of the microparticles of the microparticle composition have an average particle size of less than about 5 microns prior to the addition the A2ARA active agent, when measured by the standard techniques. In other embodiments, at least about 70%, at least about 90%, at least about 95%, or at least about 99% of the microparticles of the compositions of the invention, have a particle size of less than the effective average, by weight, i.e., less than about 5 microns. Particle size is determined by conventional particle size measuring techniques well known to those skilled in the art. Such techniques include, for example, sedimentation field flow fractionation, photon correlation spectroscopy, light scattering, dynamic light scattering, light diffraction, and disk centrifugation.

The negative charge density of the microparticles of the invention can be quantified by "zeta potential." The zeta potential of the microparticles having a negative surface charge is typically measured in an aqueous suspension of the particles at a pH of from 4 to 10, preferably from 5 to 8. Preferably, the microparticles or nanoparticles produced by the methods of the invention may have a zeta potential of from about −20 mV to about −200 mV, preferably from about −30 mV to about −100 mV, most preferably from −35 mV to −85 mV. A zeta potential more negative than about −40 mV are referred to herein as "highly negatively charged particles". The microparticles described herein include an adenosine receptor antagonist. Adenosine receptor antagonists can recognize multiple adenosine receptor subtypes (i.e., adenosine Ai receptor antagonist, adenosine A2A receptor antagonist, adenosine A2B receptor antagonist, or adenosine A3 receptor antagonist), or can be selective for one or more one or more of the adenosine receptor subtypes. In some embodiments, the adenosine receptor antagonist can specifically antagonize adenosine receptor A2A. In some embodiments, the antagonist is selective for adenosine receptor A2A. The adenosine receptor antagonists described herein can disrupt adenosine function and/or responsiveness in a subject.

As used herein, an "adenosine 2a receptor antagonist (A2ARA)" refers to an antagonist molecule that specifically binds the adenosine 2a receptor. The terms "specific to/for", "specific binding", "binds specifically to" are used interchangeably herein and refer to the ability of the antagonist to discriminate between the adenosine 2a receptor and an unrelated receptor as determined in accordance with methods known in the art such as, selectively profiling using cell-based assays. Any molecule that is an antagonist at an Ata adenosine receptor can be useful in the methods of this invention. Examples include, but are not limited to, a small molecule antagonist, a gene therapy agent, a ribozyme, an antisense oligonucleotide, or another catalytic nucleic acid that selectively binds mRNA encoding an adenosine receptor, and agents that reduce total levels of adenosine in a tissue including but not limited to an antibody, an enzyme, a protein or peptide, a fusion protein. Preferably, the A2ARA is selected from a small molecule.

Examples of preferred A2ARA include, but are not limited to: caffeine, theophylline, 8-phenyl theophylline, SCH58261, istradefylline, pyrazolo[4,3-e]-1,2,4-triazolo[1,5-c]pyrimidines or substituted derivatives thereof (e.g., methoxy biaryl or quinoline substitutions), SCH412348, SCH420814, fused heterocyclic pyrazolo[4,3-e]-1,2,4-triazolo[1,5-c] pyrimidines or substituted derivatives thereof (e.g., tetrahydroisoquinoline or azaisoquinoline derivatives), aryl piperazine substituted 3H-[1,2,4]-triazolo[5,1-i]purin-5-amines, arylindenopyrimidines, arylindenopyrimidines or substituted derivatives thereof, pyrazolo[4,3-e]-1,2,4-trizolo[4,3-c]pyrimidon-3-one and thiazolotriazolopyrimidines, 1,2,4-triazolo[1,5-c]pyrimidines or substituted derivatives thereof, purinones or substituted derivatives thereof, thieno[3,2-d]pyrimidines, pyrazolo[3,4-d]pyrimidines, and 6-arylpurines, benzyl substituted triazolo[4,5-d]pyrimidines, triazolo-9H-purines, aminomethyl substituted thieno[2,3- djpyrimidines, 2-Aminoimidazopyridines, 4-morpholino-benzothiazoles or substituted derivatives thereof, 4-Aryl and 4-morpholino substituted benzofurans, pyridone substituted pyrazines, heterocyclic substituted 2-amino-thiazoles, trisubstituted pyrimidines, piperazine substituted pyrimidine acetamides, acylaminopyrimidines, pyrimidine, pyridine, or triazine carboxamides, mixtures or combinations thereof, and pharmaceutically acceptable salts thereof.

Examples of preferred A2ARA also include, but are not limited to: of CPI-444, CVT-6883 (3-ethyl-1-propyl-8-(1-(3-trifluoromethylbenzyl)-1H-pyrazol-4-yl)-3,7-dihydropurine-2,6-dione), PBF-509, Istradefylline (KW-6002) (8-[(E)-2-(3,4-Dimethoxyphenyl)ethenyl]-1,3-diethyl-7-methylpurine-2,6-dione), Preladenant (SCH420814) (2-(2-furanyl)-7-(2-(4-(4-(2-methoxyethoxy)phenyl)-1-piperazinyl)ethyl)-7H-pyrazolo (4,3-e)(1,2,4)triazolo(1,5-c) pyrimidine-5-amine), Tozadenant (SYN115) (4-Hydroxy-N-(4-methoxy-7-morpholinobenzo[d]thiazol-2-yl)-4-methylpiperidine-1-carboxamide), Vipadenant (BIIB014) (3-(4-amino-3-methylbenzyl)-7-(2-furyl)-3H-(1,2,3)triazolo (4,5-d)pyrimidine-5-amine), HTL-1071, ST1535(2-butyl-9-methyl-8-(triazol-2-yl)purin-6-amine), SCH412348 ((7-(2-(4-difluorophenyl)-1-piperazinyl)ethyl)-2-(2-furanyl)-7H-pyrazolo(4,3-e)(1,2,4) triazolo(1,5-c)pyrimidin-5-amine), MRE2029F20, SCH442416(2-(2-furyl)-7-[3-(4-methoxyphenyl)propyl]-7H-pyrazolo[4,3-e][1,2,4]triazolo[1,5-c]pyrimidin-5-amine), MRS1754 (N-(4-Cyanophenyl)-2-[4-(2, 3,6,7-tetrahydro-2,6-dioxo-1,3-dipropyl-1H-purin-8-yl) phenoxy]-acetamide), SCH58261 (2-(2-Furanyl)-7-(2-phenylethyl)-7H-pyrazolo[4,3-e][1,2,4]triazolo[1,5-c] pyrimidin-5-amine), PSB603 a98-[4-[4-(4-Chlorophenyl) piperazide-1-sulfonyl)phenyl]]-1-propylxanthinea0, and ZM241385 (4-(2-[7-Amino-2-(2-furyl)[1,2,4]triazolo[2,3-a][1,3,5]triazin-5-ylamino]ethyl)phenol).

Preferably, the amount of the A2ARA present in the microparticles of the invention may be about 0.01-50% (w/w) of the microparticle, or about 0.05-25%, about 0.1-10%, about 0.2-5%, 0.5-3%, 1-5%, or 2-5% (w/w) of the microparticle.

Preferably, the microparticles of the invention have a zeta potential of about −40 mV or lower, about −35 mV or lower, about −30 mV or lower, about −25 mV or lower, or about −20 mV or lower. Most preferably the microparticles have a negative zeta potential of about −35 mV or lower.

Preferably, the microparticles or nanoparticles have a zeta potential of about −25 mV or lower, about −30 mV or lower, about −35 mV or lower, −40 mV or lower, −45 mV or lower, or about −50 mV or lower. Such as −40 mV to −65 mV.

The microparticles therefore preferably comprise a pharmaceutically acceptable negatively charged agent to increase the negative surface charge of the microparticles. Although the negative charge to be incorporated into the microparticles can be, for example, in the form of a carboxylate, sulfonate, nitrate, fluorate, chloride, iodide, persulfate, and many other negatively charged chemical groups, the most preferred is carboxylate. Thus, in certain embodiments, the negative charge is mainly, mostly, or exclusively conferred by carboxyl groups. Preferably, the pharmaceutically acceptable negatively charged agent is selected from the group consisting of polyacrylic acid (PAA) and hyaluronic acid (HA), and analogs or derivatives thereof, or a combination/mixture thereof. The carboxyl group can be from, for example, the PLGA, from the poly acrylic acid, and/or from the hyaluronic acid. Such an agent is preferably a pharmaceutically acceptable carboxyl-containing agent, such as one useful for producing PLGA microparticles with additional carboxyl groups on the surface. Preferably carboxy-containing agents include but are not limited to: hyaluronic acid or analogs or derivatives thereof, gelatin polysaccharides, hydroxyethylmethacrylic acid, polyacrylic acid, polymethacrylic acid, amino acids, or their salts, derivatives, copolymers and mixtures thereof. Preferably, the pharmaceutically acceptable negatively charged agent may cover the surface of the microparticles or nanoparticles, and/or be at least partially incorporated into said microparticles or nanoparticles to increase negative surface charges on the microparticles or nanoparticles.

The amount of the pharmaceutically acceptable negatively charged agent used in the current invention is from 0.01% to 30%, preferably from 0.1% to 15%, based on the weight of the pharmaceutically acceptable polymer (such as PLGA) used in the formulation.

Another aspect of the invention provides a method of producing a pharmaceutical formulation comprising the A2ARA, and a pharmaceutically acceptable polymer, wherein the pharmaceutically acceptable polymer encapsulates the A2ARA molecule to form particulates, the method being a single emulsion process comprising: (a) dissolving the A2ARA along with a pharmaceutically acceptable polymer in a first solvent to form a polymer-A2ARA solution; (b) emulsifying the polymer-A2ARA solution in a second solvent to form an emulsion, wherein the first solvent is not miscible or only partially miscible with the second solvent; and (c) removing the first solvent to form the particulates. Methods of producing negatively charged particles may also be found in US Patent Publication 2016/0310426, incorporated herein by reference.

Preferably, in step (a), the A2ARA is dissolved in a first portion of the first solvent to form a solution, before being mixed with a separately prepared polymer solution in a second portion of the first solvent.

Preferably, the polymer-A2ARA solution further comprises a surfactant. The surfactants that can be used for the preparation of the subject microparticles include, but are not limited to: polyvinyl alcohol, polyvinylpyrrolidone, Tween series, Pluronic series, Poloxamer series, Triton X-100, etc. Additional suitable surfactants are provided herein below. Preferably, a surfactant is dissolved in the second solvent before step (b).

Preferably, the method further comprises dissolving or dispersing an additional active pharmaceutical ingredient (API) in the second solvent before forming the emulsion.

Preferably, the method further comprises dissolving or dispersing a first additional API (other than the A2ARA) in the first solvent and dissolving or dispersing a second additional API (other than the A2ARA) in the second solvent.

Preferably, emulsification is performed using a method selected from the group consisting of: sonication, stirring, homogenization, microfluidization and combination thereof.

Preferably, the method further comprises adsorbing or conjugating a biologic or a chemical entity to the surface of said particles of the A2ARA.

Preferably the invention also provides a method of producing a pharmaceutical formulation comprising an A2ARA, and a pharmaceutically acceptable polymer, wherein the pharmaceutically acceptable polymer encapsulates the A2ARA molecules to form particulates, the method being a double emulsion process comprising: (a) dissolving an A2ARA chemical along with a pharmaceutically acceptable polymer in a first solvent to form a polymer-A2ARA solution; (b) adding a small amount (e.g., 0.5% (v/v), 1% (v/v), 5% (v/v)) of a second solvent to the polymer-A2ARA solution to form a mixture, wherein the first solvent is not miscible or only partially miscible with the second solvent; (c) emulsifying the mixture to form a first emulsion; (d) emulsifying the first emulsion in a third solvent to form a second emulsion; and, (e) removing the first solvent to form said particulates.

Preferably, the second and the third solvents are the same solvent. Preferably, the second and the third solvents are both water. Preferably, the third solvent further comprises a surfactant. Preferably, the surfactant is selected from the group consisting of: detergents, wetting agents, emulsifiers, foaming agents, and dispersants. Preferably, the surfactant is polyvinyl alcohol (PVA).

Preferably, the method further comprises dissolving or dispersing an additional API in the second solvent before forming the first emulsion. Preferably, the A2ARA compound is dissolved in the second solvent of Step (b) instead of in the first solvent of Step (a). Preferably, the method further comprises dissolving or dispersing a first additional API (other than the A2ARA) in the first solvent and dissolving or dispersing a second additional API (other than the A2ARA) in the second solvent.

Preferably, emulsification is performed using a method selected from the group consisting of: sonication, stirring, homogenization, microfluidization and combination thereof.

Preferably, the method further comprises adsorbing or conjugating a biologic or a chemical entity to the surface of said A2ARA particles.

Preferably, the first solvent is not miscible with water, or is selected from the group consisting of ethyl acetate, dichloromethane, and chloroform.

Preferably, a water-miscible solvent is mixed with a non-water-miscible solvent as a co-solvent for the dissolution of the polymer or the A2ARAs or both.

Preferably, the second solvent is water, or the third solvent is water.

Preferably, the polymer solution has a concentration selected from the group consisting of: 1 µg/mL-1 g/mL (w/w), 1 mg/mL-500 mg/mL (w/w), and 10 mg/mL-250 mg/mL (w/w).

Preferably, the invention also provides a method of producing a pharmaceutical formulation comprising an A2ARA, and a pharmaceutically acceptable polymer, wherein the pharmaceutically acceptable polymer encapsulates the A2ARA molecules to form particulates, the method being a precipitation process comprising: (1) dissolving the A2ARA in a first solvent along with a pharmaceutically acceptable polymer; (2) optionally adding to the first solvent a first solution comprising a surface stabilizer to form a formulation; and, (3) precipitating the formulation from step (2) into a second solution containing the surface stabilizer in a second solvent, wherein the second solvent is miscible with the first solvent and is a non-solvent for both the polymer and the A2ARA. Preferably, the first solvent is selected from the group consisting of: DMSO, DMF, acetone, alcohols, acetonitrile, and THF. Preferably, the second solvent is selected from the groups consisting of: water, methanol, ethanol, isopropyl alcohol, benzyl alcohol. In certain embodiments, the second solvent is water. Preferably, the method further comprises removing unwanted stabilizer or any impurity, if present, by centrifugation, dialysis or diafiltration.

The present invention also provides methods for enhancing an immune response in a patient in need thereof. The method comprises administering a therapeutically effective amount of an A2ARA microparticle composition of the invention to a patient in need thereof. Preferably the patient is need of anti-cancer immunotherapy.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease. A therapeutically effective amount of a combination of several active ingredients may be a therapeutically effective amount of each of the active ingredients. Alternatively, to reduce the side effects caused by the treatment, a therapeutically effective amount of a combination of several active ingredients may be amounts of the individual active ingredients that are effective to produce an additive, or synergistic effect, and that in combination are therapeutically effective, but which may be sub-therapeutic amounts of one or several of the active ingredients if they were used alone.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

The present invention also provides a method of treating cancer in a subject in need thereof comprising administering a therapeutically effective amount of a microparticle A2ARA composition described herein. In certain embodiments, the cancer includes breast cancer, pancreatic cancer, lung cancer, skin cancer, bladder cancer, blood cancer, kidney cancer, brain cancer, glioblastoma, esophagus cancer, stomach cancer, and colon cancer.

The methods of treating cancer in accordance with the invention include methods of treating a cancerous tumor, including but not limited to, solid tumors, comprising the step of injecting or implanting the microparticles of the invention into the tumor microenvironment.

The methods of treating cancer in accordance with the invention include methods of treating a tumor comprising the step of intratumorally injecting the microparticles or implanting the microparticles of the invention.

As used herein, "treatment" (and grammatical variations thereof such as "treat" or "treating") refers to clinical intervention to alter the natural course of a disease in the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

In some embodiments, combinations of the invention are used to delay development of a disease or to slow the progression of a disease.

The microparticle compositions of the invention can be used to treat, prevent, manage and slow the spread of cancer as well as other abnormal cell proliferation-associated diseases in a patient. In certain embodiments, the invention provides methods to treat carcinomas, include tumors arising from epithelial tissue, such as glands, breast, skin, and linings of the urogenital, digestive, and respiratory systems. Lung, cancer and prostate cancers can be treated or prevented. Breast cancers that can be treated or prevented include both invasive (e.g., infiltrating ductal carcinoma, infiltrating lobular carcinoma infiltrating ductal & lobular carcinoma, medullary carcinoma, mucinous (colloid) carcinoma, Paget's disease, papillary carcinoma, tubular carcinoma, adenocarcinoma (NOS) and carcinoma (NOS)) and non-invasive carcinomas (e.g., intraductal carcinoma, lobular carcinoma in situ (LCIS), intraductal & LCIS, and papillary carcinoma). The present invention can also be used to treat or prevent metastatic breast cancer. Non-limiting examples of metastatic breast cancer include bone, lung and liver cancer. Prostate cancers that can be treated or prevented with the methods described herein include localized, regional and metastatic prostate cancer. Localized prostate cancers include A1-A2, T1a-T1b, T1c, B0-B2 or T2a-T2c. C1-C2 or T3a-N0, prostate cancers extending beyond the prostate but without lymph node involvement, are also contemplated. Regional prostate cancers include D1 or N1-M0, while metastatic prostate cancers include D2 or M1. Metastatic prostate cancers include bone and brain cancers.

Methods are provided to treat or prevent abnormal cell proliferation using $A_{2a}$ receptor antagonists in combination or alternation with a cell-based vaccine. In certain of these embodiments, the cell-based vaccine is based on cells that match the tumor to be prevented. For example, if a patient is suffering from, or at risk of suffering from, a prostate cancer, the cell-based vaccine will be based on a prostate cancer tumor cell. In these instances, the cell is typically irradiated or otherwise prevented from replicating. In particular embodiments, the cell is genetically modified to secrete a colony stimulating factor.

Other cancers that can be treated or prevented with the present invention include, but are not limited to, cancers of the bowel, bladder, brain, cervix, colon, rectum, esophagus, eye, head and neck, liver, kidney, larynx, lung, skin, ovary, pancreas, pituitary gland, stomach, testicles, thymus, thyroid, uterus, and vagina as well as adrenocortical cancer, carcinoid tumors, endocrine cancers, endometrial cancer, gastric cancer, gestational trophoblastic tumors, islet cell cancer, and mesothelioma.

Lymphomas that can be treated or prevented with the invention include tumors arising from the lymph or spleen, which can cause excessive production of lymphocytes, including both Hodgkin's disease and Non-Non-Hodgkin's lymphoma. The term "Hodgkin's Disease" is intended to include diseases classified as such by the REAL and World Health Organization (WHO) classifications known to those of skill in the art, including classical Hodgkin's disease (i.e., nodular sclerosis, mixed cellularity, lymphocyte depletion or lymphocyte rich) or lymphocyte predominance Hodgkin's disease. The term "Non-Hodgkin's lymphoma" is used to refer 30 lymphomas classified by WHO (Harris N L et al. (2000) Lymphoma classification-from controversy to consensus: the REAL and WHO Classification of lymphoid neoplasms. *Ann Oncol.* 11(suppl 1):S3-S10), including but not limited to: B-cell non-Hodgkin's lymphomas such as small lymphocytic lymphoma (SLL/CLL), mantle cell lymphoma (MCL), follicular lymphoma marginal zone lymphoma (MZL), extranodal (MALT lymphoma), nodal (Monocytoid B-cell lymphoma), splenic, diffuse large cell lymphoma, burkitt's lymphoma and lymphoblastic lymphoma. T-cell non-Hodgkin's lymphoma's such as lymphoblastic lymphomas, peripheral T-cell lymphoma. Hepatosplenic gamma-delta T-cell lymphoma, subcutaneous panniculitis-like lymphoma, angioimmunoblastic T-cell lymphoma (AILD), extranodal NK/T cell lymphoma, nasal type, intestinal T-cell lymphoma (+/−enteropathy associated) (EATL), adult T-cell leukemia/lymphoma (HTLV-1 associated), mycosis fungoides/Sezary syndrome, anaplastic large cell lymphoma (ALCL), including both primary cuteous and primary systemic types.

Leukemias that can be treated or prevented with the present invention include but are not limited to myeloid and lymphocytic (sometimes referred to as B or T cell leukemias) or myeloid leukemias, both chronic and acute. The myeloid leukemias include chronic myeloid leukemia (CML) and acute myeloid leukemia (AML) (i.e., acute nonlymphocytic leukemia (ANLL)). The lymphocytic leukemias include acute lymphocytic leukemia (ALL), chronic lymphocytic leukemia (CLL) (i.e., chronic granulocytic leukemia) and hairy cell leukemia (HCL). Sarcomas that can be treated or prevented with the present invention include both bone and soft-tissue sarcomas of the muscles, tendons, fibrous tissues, fat, blood vessels nerves, and synovial tissues. Non-limiting examples include fibrosarcomas, rhabdomyosarcomas, liposarcomas, synovial sarcomas, angiosarcomas, neurofibrosarcomas, gastrointestinal stroma tumors, Kaposi's sarcoma, Ewing's sarcoma, alveolar soft-part sarcoma, angiosarcoma, dermatofibrosarcoma protuberans, epithelioid sarcoma, extraskeletal chondrosarcoma, extraskeletal osteosarcoma, fibrosarcoma, leiomyosarcoma, liposarcoma, malignant fibrous histiocytoma, malignant hemangiopericytoma, malignant mesenchymoma, malignant schwannoma, malignant peripheral nerve sheath tumor, parosteal osteosarcoma, peripheral neuroectodermal tumors, rhabdomyosarcoma, synovial sarcoma, and sarcoma, NOS.

Diseases of abnormal cell proliferation other than cancer can be treated or prevented with the present invention. Diseases association with the abnormal proliferation of vascular smooth muscle cells include, as a non-limiting example, benign tumors. Non-limiting examples of benign tumors include benign bone, brain and liver tumors.

Preferably, the invention also provides combination therapy with the microparticles of the invention and other anti-cancer treatments and anti-cancer agents including, but not limited to: other anti-cancer immunotherapies such as administration of checkpoint inhibitors, other immune modulators (e.g., immune inhibitors and immune enhancers), radiation therapy and chemotherapy.

Other diseases associated with abnormal cell proliferation include, for example, atherosclerosis and restenosis. Diseases associated with abnormal proliferation of over-proliferation and accumulation of tissue mast cells are also included, such as cutaneous mastocytosis (CM) and Urticaria pigmentosa. Diseases associated with abnormal proliferation of xesangial cell proliferation are also contemplated, including but not limited to IgA nephropathy, membranoproliferative glomerulonephritis (GN), lupus nephritis and diabetic nephropathy.

Psoriasis can be treated or prevented by the present invention, including but not limited to, plaque psoriasis, guttate psoriasis, inverse psoriasis, seborrheic psoriasis, nail psoriasis, generalized erythrodermic psoriasis (also called psoriatic exfoliative erythroderm), pustular psoriasis, and Von Zumbusch psoriasis.

The present invention can also be used to treat or prevent lymphangiomyomatosis (LAM), as well as other diseases associated with abnormal cell proliferation known to those skilled in the art.

The A2ARA microparticle compositions described herein can be administered to a subject via any conventional means including, but not limited to, orally, rectally, ocularly, parenterally (e.g., intravenous, intramuscular, or subcutaneous), intracisternally, intracranially, pulmonary, intravaginally, intraperitoneally, locally (e.g., powders, ointments or drops), or as a buccal or nasal spray. Preferably, the microparticle composition is administered intratumorally or to the tumor microenvironment by injection or by implantation into at least part of the tumor or the tumor microenvironment. The term "intratumorally" is intended to include administration into a lesion, i.e., intralesionally.

As used herein, the term "subject" is used to mean an animal, preferably a mammal, including a human or non-human. The terms patient and subject may be used herein interchangeably.

The microparticle compositions described herein can be formulated into any suitable dosage form, including but not limited to liquid dispersions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The A2ARA microparticle compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffeting agents.

Liquid microparticle composition include dosage forms for oral administration include pharmaceutically acceptable emulsions, solutions, suspensions, syrups, and elixirs. The liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

The following non-limiting examples further illustrate the invention.

EXAMPLES

Example 1

Preparation of Nanoparticles Containing SCH442416 (2-(2-furyl)-7-[3-(4-methoxyphenyl) propyl]-7H-pyrazolo[4,3-e] [1,2,4] triazolo[1,5-c] pyrimidin-5-amine) a Highly Selective A2ARA).

Approximately 5 mg of SCH442416 was dissolved in 8 mL of ethyl acetate. Such solution was sonicated for 1 minute to ensure complete dissolution. Approximately 200 mg of poly (lactic-co-glycolic acid) (PLGA) was dissolved in the same 8 mL SCH solution. The resulting solution was poured into a 4-oz glass jar containing 40 mL of 0.5% polyvinyl alcohol (PVA) solution saturated with ethyl acetate. The mixture was then immediately homogenized using an IKA roto stator at 23,800 rpm for 1 minute. The resulting emulsion was transferred to a 100 mL beaker and stirred magnetically at 610 rpm for 3 hours. Once the particles were formed and hardened, the emulsion was washed with 100 mL of distilled water three times using tangential flow filtration and was freeze-dried. The particles obtained were found to have an average diameter of 555 nm.

Example 2

Preparation of Negatively Charged Nanoparticles Containing SCH442416 and a Fluorescent Dye Approximately 5 mg of SCH442416 (SCH) was dissolved in 8 mL of ethyl acetate. Such solution was sonicated for 1 minute to ensure complete dissolution. Approximately 200 mg of poly (lactic-co-glycolic acid) (PLGA) was dissolved in the same 8 mL SCH solution together with 2 mg of Coumarin-6. The resulting solution was poured into a 4-oz glass jar containing 40 mL of 0.5% polyvinyl alcohol (PVA) solution saturated with ethyl acetate. The mixture was then immediately homogenized using an IKA roto stator at 23,800 rpm for 1 minute. The resulting emulsion was transferred to a 100 mL beaker and stirred magnetically at 610 rpm for 3 hours. Once the particles were formed and hardened, the emulsion was washed with 100 mL of distilled water three times using tangential flow filtration and was freeze-dried. The particles obtained were found to have an average diameter of 555.4 nm.

Example 3

Preparation of Highly Negatively Charged Nanoparticles Containing SCH442416

Approximately 5 mg of SCH442416 (SCH) was dissolved in 8 mL of ethyl acetate. Such solution was sonicated for 1 minute to ensure complete dissolution. Approximately 200 mg of poly (lactic-co-glycolic acid) (PLGA) was dissolved in the same 8 mL SCH solution. The resulting solution was poured into a 4-oz glass jar containing 40 mL of 0.5% polyvinyl alcohol (PVA) solution saturated with ethyl acetate and 120 mg of 35 wt. % poly (acrylic acid) solution. The mixture was then immediately homogenized using an IKA roto stator at 24000 rpm for 1 minute. The resulting emulsion was transferred to a 100 m L beaker and stirred magnetically at 610 rpm for 3 hours. Once the particles were formed and hardened, the emulsion was washed with 100 mL of distilled water three times using tangential flow filtration and was freeze-dried. The particles obtained were found to have an average diameter of 525.4 nm and zeta potential of −45.8 mV.

Example 4

Preparation of Highly Negatively Charged Nanoparticles Containing SCH442416 and a Lipophilic Fluorescent Dye DiD' Oil Approximately 5 mg of SCH-442416 (SCH) was dissolved in 8 mL of ethyl acetate. Such solution was sonicated for 1 minute to ensure complete dissolution. Approximately 200 mg of poly (lactic-co-glycolic acid) (PLGA) was dissolved in the same 8 mL SCH solution together with 2 mg of the DiD' oil: DiIC18(5) oil (1,1'-Dioctadecyl-3,3,3',3'-Tetramethylindodicarbocyanine Perchlorate). The resulting solution was poured into a 4-oz glass jar containing 40 mL of 0.5% polyvinyl alcohol (PVA) solution saturated with ethyl acetate and 120 mg of 35 wt.% poly (acrylic acid) solution. The mixture was then immediately homogenized using an IKA roto stator at 24000 rpm for 1 minute. The resulting emulsion was transferred to a 100 mL beaker and stirred magnetically at 610 rpm for 3 hours. Once the particles were formed and hardened, the emulsion was washed with 100 mL of distilled water three times using tangential flow filtration and was freeze-dried. The particles obtained were found to have an average diameter of 598.4 nm and a zeta potential of −46.7 mV.

Example 5

Preparation of Highly Negatively Charged Nanoparticles Containing SCH58261 (2-(Furan-2-yl)-7-phenethyl-7H-pyrazolo[4,3-e] [1,2,4] triazolo [1,5-c] pyrimidin-5-amine) a Highly Selective A2ARA).

Approximately 4 mg of SCH58261 (SCH) was dissolved in 0.25 mL of dimethyl sulfoxide (DMSO). Such solution was sonicated for 1 minute to ensure complete dissolution. Approximately 200 mg of poly (lactic-co-glycolic acid) (PLGA) was dissolved in the 7.75 mL of ethyl acetate and mixed with the SCH/DMSO solution. The resulting solution was poured into a 4-oz glass jar containing 40 mL of 0.5% polyvinyl alcohol (PVA) solution saturated with ethyl acetate and 120 mg of 35 wt. % poly (acrylic acid) solution. The mixture was then immediately homogenized using an IKA roto stator at 25000 rpm for 1 minute. The resulting emulsion was transferred to a 100 mL beaker and stirred magnetically at 610 rpm for 3 hours. Once the particles were formed and hardened, the emulsion was washed with 100 mL of distilled water three times using tangential flow filtration and was freeze-dried. The particles obtained were found to have an average diameter of 561.5 nm and a zeta potential of −44.8 mV.

Example 6

Preparation of Highly Negatively Charged Micropartices (1-1.5 μm) Containing SCH58261 and a Lipophilic Fluorescent Dye DiR'

Approximately 2.5 mg of SCH58261 (SCH) was dissolved in 0.25 mL of dimethyl sulfoxide (DMSO). Such solution was sonicated for 1 minute to ensure complete dissolution. Approximately 100 mg of poly (lactic-co-glycolic acid) (PLGA) was dissolved in the 3 mL of ethyl acetate together with 0.2 mg of the DiR' dye: DiIC18(7) (1,1'-Dioctadecyl-3,3,3',3'-Tetramethylindotricarbocyanine Iodide). The PLGA/dye solution was added and mixed with the SCH solution. The resulting solution was poured into a 15 mL glass vial containing 10 mL of 1.0% polyvinyl alcohol (PVA) solution saturated with ethyl acetate and 70 mg of 35 wt. % poly (acrylic acid) solution. The mixture was then immediately homogenized using a tissue mixer at maximum speed for 30 seconds. The resulting emulsion was transferred to a 50 mL beaker and stirred magnetically at 400 rpm for 3 hours. Once the particles were formed and hardened, the particles were spun down at 5300 rcf for 10 minutes using Heraeus Biofuge 22R centrifuge and decanted all the supernatant. The pellets were resuspended and washed with 50 mL of distilled water and the particles were spun down again at 5300 rcf for 10 minutes. The particles obtained were found to have an average diameter of 1.452 μm and a negative zeta potential of −41.3 mV.

Example 7

Preparation of Microparticles (1-1.5 μm) Containing SCH58261 and a Lipophilic Fluorescent Dye DiR'

Approximately 4 mg of SCH58261 (SCH) was dissolved in 0.3 mL of dimethyl sulfoxide (DMSO). Such solution was sonicated for 1 minute to ensure complete dissolution.

Approximately 200 mg of poly (lactic-co-glycolic acid) (PLGA) was dissolved in the 10 mL of ethyl acetate together with the DiR' dye (0.2 mg). The PLGA/dye solution was added and mixed with the SCH solution. The resulting solution was poured into a 50 mL conical tube containing 30 mL of 0.1% polyvinyl alcohol (PVA) solution. The mixture was then immediately homogenized using an IKA roto stator at 13,000 rpm for 2 minutes. The resulting emulsion was transferred to a 100 mL beaker and stirred magnetically at 400 rpm for 5 hours. Once the particles were formed and hardened, they were spun down at 5,300 rcf for 10 minutes using Heraeus Biofuge 22R centrifuge and decanted all the supernatant. The particles were resuspended and washed with 50 mL of distilled water and were spun down again at 5,300 rcf for 5 minutes. The particles obtained were found to have an average diameter of 1.299 μm and a zeta potential of −33.1 mV.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A composition comprising microparticles wherein the microparticles comprise at least one adenosine 2a receptor antagonist (A2ARA), at least one pharmaceutically acceptable polymer and at least one pharmaceutically acceptable negatively charged agent wherein the microparticles have a highly negatively charged surface and a zeta potential of less than about -40 mV.

2. The composition of claim 1, wherein the at least one pharmaceutically acceptable polymer is PLGA.

3. A method of treating cancer in a patient in need thereof comprising administering a therapeutically effective amount of the microparticle composition of claim 1.

4. A method of enhancing an immune response in a patient in need thereof, said method comprising administering a therapeutically effective amount of an A2ARA microparticle composition of claim 1 to a patient.

5. The method of claim 3, wherein the patient is in need of immunotherapy for the treatment of cancer.

6. The method of claim 3, further comprising administering a checkpoint inhibitor, chemotherapy, radiation, or any combination thereof.

7. A method of treating a cancerous tumor comprising the step of intratumorally injecting or intratumorally implanting the microparticles of claim 1.

8. A method of treating a cancerous tumor comprising the step of injecting the microparticles of claim 1 into the tumor microenvironment.

9. A method of sustained delivery of A2ARA to a tumor microenvironment comprising the step of injecting the microparticles of claim 1 into the tumor microenvironment.

10. The composition of claim 1, wherein the effective particles size of the microparticles are about 1 nm to about 10 μm.

11. The composition of claim 10, wherein the effective particle size of the microparticles is selected from 900 nm or lower.

12. The composition of claim 1 formulated for administration to a subject orally, rectally, ocularly, parenterally, intracisternally, intracranially, pulmonarily, intravaginally, intraperitoneally, topically, intratumorally, by injection into the tumor microenvironment, buccally or by nasal spray.

13. The composition of claim 2, wherein the pharmaceutically acceptable negatively charged agent is polyacrylic acid.

14. A composition comprising microparticles wherein the microparticles comprise at least one adenosine 2a receptor antagonist (A2ARA), PLGA and polyacrylic acid wherein the microparticles have a highly negatively charged surface and a zeta potential of less than about -40 mV.

15. The composition of claim 14, wherein the effective particle size of the microparticles is about 1 nm to about 10 μm.

16. The composition of claim 14, wherein the effective particle size of the microparticles is selected from 900 nm or lower.

17. The composition of claim 14, wherein the effective particle size of the microparticles is selected from 500 nm or lower.

18. The composition of claim 14, wherein the adenosine 2a receptor antagonist is (2-(2-furyl)-7-[3-(4-methoxyphenyl) propyl]-7H-pyrazolo[4,3-e] [1,2,4] triazolo[1,5-c] pyrimidin-5-amine).

19. The composition of claim 1, wherein the adenosine 2a receptor antagonist is (2-(2-furyl)-7-[3-(4-methoxyphenyl) propyl]-7H-pyrazolo[4,3 -e] [1,2,4] triazolo[1,5-c] pyrimidin-5-amine).

\* \* \* \* \*